US007981431B2

(12) United States Patent
Chen et al.

(10) Patent No.: US 7,981,431 B2

(45) Date of Patent: Jul. 19, 2011

(54) CONSENSUS DENGUE VIRUS ENVELOPE PROTEIN DOMAIN III POLYPEPTIDES (CED III) AND THEIR METHODS OF USE

(75) Inventors: Hsin-Wei Chen, Zhunan Town (TW); Chih-Hsiang Leng, Zhunan Town (TW); Pele Choi-Sing Chong, Zhunan Town (TW)

(73) Assignee: National Health Research Institutes, Zhunan Town, Miaoli County (TW)

( * ) Notice: Subject to any disclaimer, the term of this patent is extended or adjusted under 35 U.S.C. 154(b) by 185 days.

(21) Appl. No.: 12/156,908

(22) Filed: Jun. 4, 2008

(65) Prior Publication Data

US 2009/0074781 A1 Mar. 19, 2009

Related U.S. Application Data

(60) Provisional application No. 60/942,703, filed on Jun. 8, 2007.

(51) Int. Cl.

| | |
|---|---|
| ***A61K 39/12*** | (2006.01) |
| ***C12Q 1/70*** | (2006.01) |
| ***B01L 3/00*** | (2006.01) |

(52) U.S. Cl. .......................... 424/218.1; 435/5; 422/430

(58) Field of Classification Search ........................ None
See application file for complete search history.

(56) References Cited

OTHER PUBLICATIONS

Yauch, L. E., and S. Shresta, 2008, Mouse models of dengue virus infection and disease, Antiviral Res. 80:87-93.*

Malavige, G. N., et al., 2004, Dengue viral infections, Postgraduate Medical J., 80:588-601.*

Stephenson, J. R., 2005, Understanding dengue pathogenesis: implications for vaccine design, Bull. World Health Org. 83:308-314.*

Whiltehead, S. S., et al., 2007, Prospects for a dengue virus vaccine, Nat. Rev. Microbiol. 5:S18-S28.*

* cited by examiner

*Primary Examiner* — Jeffrey Parkin

(74) *Attorney, Agent, or Firm* — Alston and Bird LLP

(57) ABSTRACT

A consensus peptide sequence designed for domain III of the envelope proteins of four serotypes of dengue virus and used in a vaccine against multiple serotypes of dengue virus is disclosed. The vaccine is able to elicit cross-neutralization antibody responses against multiple serotypes of dengue virus.

17 Claims, 6 Drawing Sheets

A
DEN-1 consensus
P17763
P27910
P27909
P33478
P27912
P27913
B
DEN-2 consensus
P07564
P12823
Q9WDA6
P14337
P29990
P29991
P14340
C
DEN-3 consensus
P27915
Q99D35
Q5UB51
Q6YMS3
Q6YMS4
D
DEN-4 consensus
P09866
Q5UCB8
Q2YHF0
Q2YHF2
Q58HT7
E
DEN consensus
DEN-1 consensus
DEN-2 consensus
DEN-3 consensus
DEN-4 consensus

SEQUENCE LISTING

```
<160> NUMBER OF SEQ ID NOS: 20

<210> SEQ ID NO 1
<211> LENGTH: 103
<212> TYPE: PRT
<213> ORGANISM: Dengue virus type 1

<400> SEQUENCE: 1

Lys Gly Met Ser Tyr Val Met Cys Thr Gly Ser Phe Lys Leu Glu Lys
1               5                   10                  15

Glu Val Ala Glu Thr Gln His Gly Thr Val Leu Val Gln Val Lys Tyr
            20                  25                  30

Glu Gly Thr Asp Ala Pro Cys Lys Ile Pro Phe Ser Ser Gln Asp Glu
        35                  40                  45

Lys Gly Val Thr Gln Asn Gly Arg Leu Ile Thr Ala Asn Pro Ile Val
    50                  55                  60

Thr Asp Lys Glu Lys Pro Val Asn Ile Glu Ala Glu Pro Pro Phe Gly
65                  70                  75                  80

Glu Ser Tyr Ile Val Val Gly Ala Gly Glu Lys Ala Leu Lys Leu Ser
                85                  90                  95

Trp Phe Lys Lys Gly Ser Ser
            100


<210> SEQ ID NO 2
<211> LENGTH: 103
<212> TYPE: PRT
<213> ORGANISM: Dengue virus type 2
```

```
<400> SEQUENCE: 2

Lys Gly Met Ser Tyr Ser Met Cys Thr Gly Lys Phe Lys Val Val Lys
1               5                   10                  15

Glu Ile Ala Glu Thr Gln His Gly Thr Ile Val Ile Arg Val Gln Tyr
            20                  25                  30

Glu Gly Asp Gly Ser Pro Cys Lys Ile Pro Phe Glu Ile Met Asp Leu
        35                  40                  45

Glu Lys Arg His Val Leu Gly Arg Leu Ile Thr Val Asn Pro Ile Val
    50                  55                  60

Thr Glu Lys Asp Ser Pro Val Asn Ile Glu Ala Glu Pro Pro Phe Gly
65                  70                  75                  80

Asp Ser Tyr Ile Ile Ile Gly Val Glu Pro Gly Gln Leu Lys Leu Asn
                85                  90                  95

Trp Phe Lys Lys Gly Ser Ser
            100


<210> SEQ ID NO 3
<211> LENGTH: 103
<212> TYPE: PRT
<213> ORGANISM: Dengue virus type 3

<400> SEQUENCE: 3

Lys Gly Met Ser Tyr Ala Met Cys Leu Asn Thr Phe Val Leu Lys Lys
1               5                   10                  15

Glu Val Ser Glu Thr Gln His Gly Thr Ile Leu Ile Lys Val Glu Tyr
            20                  25                  30

Lys Gly Glu Asp Ala Pro Cys Lys Ile Pro Phe Ser Thr Glu Asp Gly
        35                  40                  45

Gln Gly Lys Ala His Asn Gly Arg Leu Ile Thr Ala Asn Pro Val Val
    50                  55                  60

Thr Lys Lys Glu Glu Pro Val Asn Ile Glu Ala Glu Pro Pro Phe Gly
65                  70                  75                  80

Glu Ser Asn Ile Val Ile Gly Ile Gly Asp Lys Ala Leu Lys Ile Asn
                85                  90                  95

Trp Tyr Lys Lys Gly Ser Ser
            100


<210> SEQ ID NO 4
<211> LENGTH: 103
<212> TYPE: PRT
<213> ORGANISM: Dengue virus type 4

<400> SEQUENCE: 4

Lys Gly Met Ser Tyr Thr Met Cys Ser Gly Lys Phe Ser Ile Asp Lys
1               5                   10                  15

Glu Met Ala Glu Thr Gln His Gly Thr Thr Val Val Lys Val Lys Tyr
            20                  25                  30

Glu Gly Ala Gly Ala Pro Cys Lys Val Pro Ile Glu Ile Arg Asp Val
        35                  40                  45

Asn Lys Glu Lys Val Val Gly Arg Ile Ile Ser Ser Thr Pro Phe Ala
    50                  55                  60

Glu Asn Thr Asn Ser Val Thr Asn Ile Glu Leu Glu Pro Pro Phe Gly
65                  70                  75                  80

Asp Ser Tyr Ile Val Ile Gly Val Gly Asp Ser Ala Leu Thr Leu His
                85                  90                  95

Trp Phe Arg Lys Gly Ser Ser
            100
```

<210> SEQ ID NO 5
<211> LENGTH: 103
<212> TYPE: PRT
<213> ORGANISM: Artificial
<220> FEATURE:
<223> OTHER INFORMATION: consensus sequence of dengue virus
<220> FEATURE:
<221> NAME/KEY: MISC_FEATURE
<222> LOCATION: (15)..(15)
<223> OTHER INFORMATION: Xaa can be Glu, Val, Lys, Asp
<220> FEATURE:
<221> NAME/KEY: MISC_FEATURE
<222> LOCATION: (27)..(27)
<223> OTHER INFORMATION: Xaa can be Leu, Val
<220> FEATURE:
<221> NAME/KEY: MISC_FEATURE
<222> LOCATION: (28)..(28)
<223> OTHER INFORMATION: Xaa can be Isoleu, Val
<220> FEATURE:
<221> NAME/KEY: MISC_FEATURE
<222> LOCATION: (35)..(35)
<223> OTHER INFORMATION: Xaa can be Thr, Asp, Glu, Ala
<220> FEATURE:
<221> NAME/KEY: MISC_FEATURE
<222> LOCATION: (46)..(46)
<223> OTHER INFORMATION: Xaa can be Gln, Met, Glu, Arg

<400> SEQUENCE: 5

```
Lys Gly Met Ser Tyr Ala Met Cys Thr Gly Lys Phe Lys Leu Xaa Lys
1               5                   10                  15

Glu Val Ala Glu Thr Gln His Gly Thr Ile Xaa Xaa Lys Val Lys Tyr
            20                  25                  30

Glu Gly Xaa Gly Ala Pro Cys Lys Ile Pro Phe Glu Ile Xaa Asp Val
        35                  40                  45

Glu Lys Lys His Val Asn Gly Arg Leu Ile Thr Ala Asn Pro Ile Val
    50                  55                  60

Thr Asp Lys Glu Ser Pro Val Asn Ile Glu Ala Glu Pro Pro Phe Gly
65                  70                  75                  80

Asp Ser Tyr Ile Val Ile Gly Val Gly Asp Lys Ala Leu Lys Leu Asn
                85                  90                  95

Trp Phe Lys Lys Gly Ser Ser
            100
```

<210> SEQ ID NO 6
<211> LENGTH: 34
<212> TYPE: PRT
<213> ORGANISM: Artificial
<220> FEATURE:
<223> OTHER INFORMATION: synthetic peptide

<400> SEQUENCE: 6

```
Met Cys Thr Gly Lys Phe Lys Leu Glu Lys Glu Val Ala Glu Thr Gln
1               5                   10                  15

His Gly Thr Ile Leu Ile Lys Val Lys Tyr Glu Gly Asp Gly Ala Pro
            20                  25                  30

Cys Lys
```

<210> SEQ ID NO 7
<211> LENGTH: 103
<212> TYPE: PRT
<213> ORGANISM: Dengue virus type 1

<400> SEQUENCE: 7

```
Lys Gly Thr Ser Tyr Val Met Cys Thr Gly Ser Phe Lys Leu Glu Lys
1               5                   10                  15

Glu Val Ala Glu Thr Gln His Gly Thr Val Leu Val Gln Val Lys Tyr
            20                  25                  30

Glu Gly Thr Asp Ala Pro Cys Lys Ile Pro Phe Ser Thr Gln Asp Glu
        35                  40                  45

Lys Gly Val Thr Gln Asn Gly Arg Leu Ile Thr Ala Asn Pro Ile Val
    50                  55                  60

Thr Asp Lys Glu Lys Pro Val Asn Ile Glu Thr Glu Pro Pro Phe Gly
65                  70                  75                  80

Glu Ser Tyr Ile Val Val Gly Ala Gly Glu Lys Ala Leu Lys Leu Ser
                85                  90                  95

Trp Phe Lys Lys Gly Ser Ser
            100
```

<210> SEQ ID NO 8
<211> LENGTH: 103
<212> TYPE: PRT
<213> ORGANISM: Dengue virus type 1

<400> SEQUENCE: 8

```
Lys Gly Met Ser Tyr Val Met Cys Thr Gly Ser Phe Lys Leu Glu Lys
1               5                   10                  15

Glu Val Ala Glu Thr Gln His Gly Thr Val Leu Val Gln Val Lys Tyr
            20                  25                  30

Glu Gly Thr Asp Ala Pro Cys Lys Ile Pro Phe Ser Thr Gln Asp Glu
        35                  40                  45

Lys Gly Val Thr Gln Asn Gly Arg Leu Ile Thr Ala Asn Pro Ile Val
    50                  55                  60

Thr Asp Lys Glu Lys Pro Val Asn Ile Glu Thr Glu Pro Pro Phe Gly
65                  70                  75                  80

Glu Ser Tyr Ile Val Val Gly Ala Gly Glu Lys Ala Leu Lys Gln Cys
                85                  90                  95

Trp Phe Lys Lys Gly Ser Ser
            100
```

<210> SEQ ID NO 9
<211> LENGTH: 103
<212> TYPE: PRT
<213> ORGANISM: Dengue virus type 1

<400> SEQUENCE: 9

```
Lys Gly Val Ser Tyr Val Met Cys Thr Gly Ser Phe Lys Leu Glu Lys
1               5                   10                  15

Glu Val Ala Glu Thr Gln His Gly Thr Val Leu Val Gln Val Lys Tyr
            20                  25                  30

Glu Gly Thr Asp Ala Pro Cys Lys Ile Pro Phe Ser Ser Gln Asp Glu
        35                  40                  45

Lys Gly Val Thr Gln Asn Gly Arg Leu Ile Thr Ala Asn Pro Ile Val
    50                  55                  60

Ile Asp Lys Glu Lys Pro Val Asn Ile Glu Ala Glu Pro Pro Phe Gly
65                  70                  75                  80

Glu Ser Tyr Ile Val Val Gly Ala Gly Glu Lys Ala Leu Lys Leu Ser
                85                  90                  95

Trp Phe Lys Lys Gly Ser Ser
            100
```

-continued

<210> SEQ ID NO 10
<211> LENGTH: 103
<212> TYPE: PRT
<213> ORGANISM: Dengue virus type 1

<400> SEQUENCE: 10

```
Lys Gly Met Ser Tyr Val Met Cys Thr Gly Ser Phe Lys Leu Glu Lys
1               5                   10                  15

Glu Val Ala Glu Thr Gln His Gly Thr Val Leu Val Gln Val Lys Tyr
            20                  25                  30

Glu Gly Thr Asp Ala Pro Cys Lys Ile Pro Phe Ser Ser Gln Asp Glu
        35                  40                  45

Lys Gly Val Thr Gln Asn Gly Arg Leu Ile Thr Ala Asn Pro Ile Val
    50                  55                  60

Ile Asp Lys Glu Lys Pro Val Asn Ile Glu Ala Glu Pro Pro Phe Gly
65                  70                  75                  80

Glu Ser Tyr Ile Val Val Gly Ser Gly Glu Lys Ala Leu Lys Leu Ser
                85                  90                  95

Trp Phe Lys Lys Gly Ser Ser
            100
```

<210> SEQ ID NO 11
<211> LENGTH: 103
<212> TYPE: PRT
<213> ORGANISM: Dengue virus type 2

<400> SEQUENCE: 11

```
Lys Gly Met Ser Tyr Ser Met Cys Thr Gly Lys Phe Lys Ile Val Lys
1               5                   10                  15

Glu Ile Ala Glu Thr Gln His Gly Thr Ile Val Ile Arg Val Gln Tyr
            20                  25                  30

Glu Gly Asp Gly Ser Pro Cys Lys Ile Pro Phe Glu Ile Met Asp Leu
        35                  40                  45

Glu Lys Arg His Val Leu Gly Arg Leu Ile Thr Val Asn Pro Ile Val
    50                  55                  60

Thr Glu Lys Asp Ser Pro Val Asn Ile Glu Ala Glu Pro Pro Phe Gly
65                  70                  75                  80

Asp Ser Tyr Ile Ile Ile Gly Val Glu Pro Gly Gln Leu Lys Leu Asn
                85                  90                  95

Trp Phe Lys Lys Gly Ser Ser
            100
```

<210> SEQ ID NO 12
<211> LENGTH: 103
<212> TYPE: PRT
<213> ORGANISM: Dengue virus type 2

<400> SEQUENCE: 12

```
Lys Gly Met Ser Tyr Ser Met Cys Thr Gly Lys Phe Lys Val Val Lys
1               5                   10                  15

Glu Ile Ala Glu Thr Gln His Gly Thr Ile Val Ile Arg Val Gln Tyr
            20                  25                  30

Glu Gly Asp Gly Ser Pro Cys Lys Thr Pro Phe Glu Ile Met Asp Leu
        35                  40                  45

Glu Lys Arg His Val Leu Gly Arg Leu Thr Thr Val Asn Pro Ile Val
    50                  55                  60

Thr Glu Lys Asp Ser Pro Val Asn Ile Glu Ala Glu Pro Pro Phe Gly
65                  70                  75                  80
```

```
Asp Ser Tyr Ile Ile Ile Gly Val Glu Pro Gly Gln Leu Lys Leu Asp
                85                  90                  95

Trp Phe Lys Lys Gly Ser Ser
            100


<210> SEQ ID NO 13
<211> LENGTH: 103
<212> TYPE: PRT
<213> ORGANISM: Dengue virus type 2

<400> SEQUENCE: 13

Lys Gly Met Ser Tyr Ser Met Cys Thr Gly Lys Phe Lys Ile Val Lys
1               5                   10                  15

Glu Ile Ala Glu Thr Gln His Gly Thr Ile Val Ile Arg Val Gln Tyr
            20                  25                  30

Glu Gly Asp Gly Ser Pro Cys Lys Ile Pro Phe Glu Ile Met Asp Leu
        35                  40                  45

Glu Lys Arg His Val Leu Gly Arg Leu Ile Thr Val Asn Pro Ile Val
    50                  55                  60

Thr Glu Lys Asp Ser Pro Val Asn Ile Glu Ala Glu Pro Pro Phe Gly
65                  70                  75                  80

Asp Ser Tyr Ile Ile Ile Gly Ala Glu Pro Gly Gln Leu Lys Leu Asp
                85                  90                  95

Trp Phe Lys Lys Gly Ser Ser
            100


<210> SEQ ID NO 14
<211> LENGTH: 103
<212> TYPE: PRT
<213> ORGANISM: Dengue virus type 3

<400> SEQUENCE: 14

Lys Gly Met Ser Tyr Ala Met Cys Leu Asn Thr Phe Val Leu Lys Lys
1               5                   10                  15

Glu Val Ser Glu Thr Gln His Gly Thr Ile Leu Ile Lys Val Glu Tyr
            20                  25                  30

Lys Gly Glu Asp Ala Pro Cys Lys Ile Pro Phe Ser Thr Glu Asp Gly
        35                  40                  45

Gln Gly Lys Ala His Asn Gly Arg Leu Ile Thr Ala Asn Pro Val Val
    50                  55                  60

Thr Lys Lys Glu Glu Pro Val Asn Ile Glu Ala Glu Pro Pro Phe Gly
65                  70                  75                  80

Glu Ser Asn Ile Val Ile Gly Ile Gly Asp Lys Ala Leu Lys Ile Asn
                85                  90                  95

Trp Tyr Arg Lys Gly Ser Ser
            100


<210> SEQ ID NO 15
<211> LENGTH: 103
<212> TYPE: PRT
<213> ORGANISM: Dengue virus type 3

<400> SEQUENCE: 15

Lys Gly Met Ser Tyr Ala Met Cys Thr Asn Thr Phe Val Leu Lys Lys
1               5                   10                  15

Glu Val Ser Glu Thr Gln His Gly Thr Ile Leu Ile Lys Val Glu Tyr
            20                  25                  30
```

-continued

```
Lys Gly Glu Asp Ala Pro Cys Lys Ile Pro Phe Ser Thr Glu Asp Gly
        35                  40                  45

Gln Gly Lys Ala His Asn Gly Arg Leu Ile Thr Ala Asn Pro Val Val
    50                  55                  60

Thr Lys Lys Glu Glu Pro Val Asn Ile Glu Ala Glu Pro Pro Phe Gly
65                  70                  75                  80

Glu Ser Asn Ile Val Ile Gly Ile Gly Asp Asn Ala Leu Lys Ile Asn
                85                  90                  95

Trp Tyr Lys Lys Gly Ser Ser
            100


<210> SEQ ID NO 16
<211> LENGTH: 103
<212> TYPE: PRT
<213> ORGANISM: Dengue virus type 4

<400> SEQUENCE: 16

Lys Gly Met Ser Tyr Thr Met Cys Ser Gly Lys Phe Ser Ile Asp Lys
1               5                   10                  15

Glu Met Ala Glu Thr Gln His Gly Thr Thr Val Val Lys Val Lys Tyr
            20                  25                  30

Glu Gly Ala Gly Ala Pro Cys Lys Val Pro Ile Glu Ile Arg Asp Val
        35                  40                  45

Asn Lys Glu Lys Val Val Gly Arg Ile Ile Ser Ser Thr Pro Leu Ala
    50                  55                  60

Glu Asn Thr Asn Ser Val Thr Asn Ile Glu Leu Glu Pro Pro Phe Gly
65                  70                  75                  80

Asp Ser Tyr Ile Val Ile Gly Val Gly Asn Ser Ala Leu Thr Leu His
                85                  90                  95

Trp Phe Arg Lys Gly Ser Ser
            100


<210> SEQ ID NO 17
<211> LENGTH: 103
<212> TYPE: PRT
<213> ORGANISM: Dengue virus type 4

<400> SEQUENCE: 17

Lys Gly Met Ser Tyr Thr Met Cys Ser Gly Lys Phe Ser Ile Asp Lys
1               5                   10                  15

Glu Met Ala Glu Thr Gln His Gly Thr Thr Val Val Lys Val Lys Tyr
            20                  25                  30

Glu Gly Ala Gly Ala Pro Cys Lys Val Pro Ile Glu Ile Arg Asp Val
        35                  40                  45

Asn Lys Glu Lys Val Val Gly Arg Val Ile Ser Ser Thr Pro Leu Ala
    50                  55                  60

Glu Asn Thr Asn Ser Val Thr Asn Ile Glu Leu Glu Pro Pro Phe Gly
65                  70                  75                  80

Asp Ser Tyr Ile Val Ile Gly Val Gly Asn Ser Ala Leu Thr Leu His
                85                  90                  95

Trp Phe Arg Lys Gly Ser Ser
            100


<210> SEQ ID NO 18
<211> LENGTH: 103
<212> TYPE: PRT
<213> ORGANISM: Dengue virus type 4
```

<400> SEQUENCE: 18

Lys Gly Met Ser Tyr Thr Met Cys Ser Gly Lys Phe Ser Ile Asp Lys
1               5                   10                  15

Glu Met Ala Glu Thr Gln His Gly Thr Thr Val Val Lys Val Lys Tyr
            20                  25                  30

Glu Gly Thr Gly Ala Pro Cys Lys Val Pro Ile Glu Ile Arg Asp Val
        35                  40                  45

Asn Lys Glu Lys Val Val Gly Arg Ile Ile Ser Ser Thr Pro Phe Ala
    50                  55                  60

Glu Asn Thr Asn Ser Val Thr Asn Ile Glu Leu Glu Pro Pro Phe Gly
65                  70                  75                  80

Asp Ser Tyr Ile Val Ile Gly Val Gly Asp Ser Ala Leu Thr Leu His
                85                  90                  95

Trp Phe Arg Lys Gly Ser Ser
            100

<210> SEQ ID NO 19
<211> LENGTH: 103
<212> TYPE: PRT
<213> ORGANISM: Dengue virus type 4

<400> SEQUENCE: 19

Lys Gly Met Ser Tyr Thr Met Cys Ser Gly Lys Phe Ser Ile Asp Arg
1               5                   10                  15

Glu Met Ala Glu Thr Gln His Gly Thr Thr Val Val Lys Val Lys Tyr
            20                  25                  30

Glu Gly Thr Gly Ala Pro Cys Lys Val Pro Ile Glu Ile Arg Asp Val
        35                  40                  45

Asn Lys Glu Lys Val Val Gly Arg Ile Ile Ser Ser Thr Pro Phe Ala
    50                  55                  60

Glu Asn Thr Asn Ser Val Thr Asn Ile Glu Leu Glu Pro Pro Phe Gly
65                  70                  75                  80

Asp Ser Tyr Ile Val Ile Gly Val Gly Asp Ser Ala Leu Thr Leu His
                85                  90                  95

Trp Phe Arg Lys Gly Ser Ser
            100

<210> SEQ ID NO 20
<211> LENGTH: 103
<212> TYPE: PRT
<213> ORGANISM: Dengue virus type 4

<400> SEQUENCE: 20

Lys Gly Met Ser Tyr Thr Met Cys Ser Gly Lys Phe Ser Ile Asp Lys
1               5                   10                  15

Glu Met Ala Glu Thr Gln His Gly Thr Thr Val Val Lys Val Lys Tyr
            20                  25                  30

Glu Gly Ala Gly Ala Pro Cys Lys Val Pro Ile Glu Ile Arg Asp Val
        35                  40                  45

Asn Lys Glu Lys Val Val Gly Arg Ile Ile Ser Ser Thr Pro Phe Ala
    50                  55                  60

Glu Tyr Thr Asn Ser Val Thr Asn Ile Glu Leu Glu Pro Pro Phe Gly
65                  70                  75                  80

-continued

```
Asp Ser Tyr Ile Val Ile Gly Val Gly Asp Ser Ala Leu Thr Leu His
                85                  90                  95

Trp Phe Arg Lys Gly Ser Ser
            100
```

CONSENSUS DENGUE VIRUS ENVELOPE PROTEIN DOMAIN III POLYPEPTIDES (CED III) AND THEIR METHODS OF USE

CROSS-REFERENCE TO RELATED APPLICATIONS

This application is related to and hereby claims the priority benefit of U.S. Provisional Application No. 60/942,703, filed Jun. 8, 2007, incorporated herein by reference.

BACKGROUND

Technical Field

The present invention generally relates to dengue virology, and more particularly to a dengue virus peptide vaccine and methods of preparing and using the same.

Dengue fever (DF) is the most important mosquito-borne disease affecting humans after malaria. Dengue fever, a self-limited febrile illness, is caused by any of four closely related serotypes of dengue viruses (DEN), dengue-1, dengue-2, dengue-3, and dengue-4, which are transmitted to humans by mosquitoes. In most cases, patients with DF have a sudden onset of fever, with severe headache, muscle and joint pains, and occasional rashes. The DF may progress to dengue hemorrhagic fever (DHF), which may show higher fever, hemorrhagic phenomena, thrombocytopenia and hemoconcentration. A small proportion of cases lead to dengue shock syndrome (DSS) which has a high mortality rate.

The diagnosis of dengue infection is usually made clinically. Serology and polymerase chain reaction (PCR) studies are available to confirm the diagnosis of dengue infection if clinically indicated. Some cases with milder symptoms, for example when no rash is present, can be misdiagnosed as a flu or other viral infection. Accurate diagnosis of dengue infection is important for proper treatment of the illness. For example, although aspirin and non-steroidal anti-inflammatory medications are often used to treat pain and fever caused by viral infection, they may aggravate the bleeding tendency associated with some dengue infections. Acetaminophen, instead of aspirin and non-steroidal anti-inflammatory medications, should be used to deal with these symptoms.

Evidence suggests that DHF is more likely to occur in patients who have secondary infections by serotypes different from the primary infection, a phenomenon also known as superinfection. This is due to antibody-dependent enhancement (ADE), which allows for increased uptake and virion replication during a secondary infection with a different strain. Therefore, any potential dengue vaccine is preferably effective against multiple serotypes, most preferably against all four serotypes. A dengue vaccine that is not effective against all four serotypes can leave the individual at risk for DHF and/or DSS.

Supportive therapy is the main treatment for DF. Oral intake of fluids, supplemented with intravenous fluids, is utilized to prevent dehydration and significant hemoconcentration.

Currently, the primary prevention of dengue virus infection mainly resides in eliminating or reducing the mosquito vector for dengue. It is desirable to develop a vaccine effective against multiple serotypes of dengue virus and a simple and more accurate diagnostic test for dengue infection. Embodiments of the present invention relate to such a vaccine and diagnostic test.

BRIEF SUMMARY

A peptide vaccine has been designed and produced according to the present invention to elicit cross-neutralization antibody responses against multiple serotypes of dengue virus.

In one general aspect, an embodiment of the present invention relates to an isolated, or recombinant, or synthetic peptide consisting essentially of SEQ ID NO:5.

In another general aspect, an embodiment of the present invention relates to an immunogenic composition. The immunogenic composition comprises a peptide consisting essentially of SEQ ID NO:5. In one embodiment, the immunogenic composition comprises a peptide consisting essentially of SEQ ID NO:5 and an adjuvant. Another embodiment of the present invention relates to a kit comprising the immunogenic composition and instructions for using the immunogenic composition to induce an immune response in a subject. Another embodiment of the present invention relates to a method of inducing an immune response in a subject. The method comprises administering to the subject an immunogenically effective amount of the immunogenic composition. Another embodiment of the present invention relates to a method of preventing a disease or a disorder associated with dengue virus in a subject. The method comprises administering to the subject a vaccination effective amount of a vaccine comprising a peptide consisting essentially of SEQ ID NO:5.

In another general aspect, an embodiment of the invention relates to an antibody that selectively binds to a peptide consisting essentially of SEQ ID NO:5. Another embodiment of the invention relates to a method of producing an antibody that selectively binds to a peptide consisting essentially of SEQ ID NO:5. The method comprises contacting a cell with the peptide consisting essentially of SEQ ID NO:5; and growing the cell under conditions that allow production of the antibody from the cell. Another embodiment of the invention relates to a therapeutic composition comprising an antibody that selectively binds to a peptide consisting essentially of SEQ ID NO:5. Another embodiment of the invention relates to a method of treating a dengue disease or disorder in a subject. The method comprises administering to the subject a therapeutically effective amount of the therapeutic composition comprising an antibody that selectively binds to a peptide consisting essentially of SEQ ID NO:5.

In yet another general aspect, embodiments of the invention relate to methods of detecting a dengue virus infection in a subject. In one embodiment, the method comprises: (a) obtaining a biological sample from the subject; (b) contacting the biological sample with an antibody that selectively binds to a peptide consisting essentially of SEQ ID NO:5; and (c) detecting the presence of an antigen in the biological sample that binds specifically to the antibody. In another embodiment, the diagnostic method comprises: (a) obtaining a biological sample from the subject; (b) contacting the biological sample with a peptide consisting essentially of SEQ ID NO:5; and (c) detecting the presence of an antibody in the biological sample that binds specifically to the peptide.

Embodiments of the invention also relate to a kit for detecting a dengue virus infection in a subject. In one example, the kit comprises a peptide consisting essentially of SEQ ID NO:5 and instructions for using the peptide to detect the dengue virus infection in the subject. In another example, the kit comprises an antibody that selectively binds to a peptide consisting essentially of SEQ ID NO:5 and instructions for using the antibody to detect the dengue infection in the subject.

Another aspect of the invention relates to a method of designing a peptide vaccine against at least one dengue virus selected from the group consisting of serotypes 1, 2, 3, and 4 of dengue virus. The method comprises: (a) determining a consensus sequence for the amino acid sequences of domain III of envelope proteins from the dengue virus; and (b) designing the peptide vaccine comprising a peptide having the consensus sequence.

Other aspects, features and advantages of the invention will be apparent from the following disclosure, including the detailed description of the invention and its preferred embodiments and the appended claims.

BRIEF DESCRIPTION OF THE SEVERAL VIEWS OF THE DRAWINGS

The foregoing summary, as well as the following detailed description of preferred embodiments of the invention, will be better understood when read in conjunction with the appended drawings. For purposes of illustrating the invention, there are shown in the drawings embodiments which are presently preferred. It should be understood, however, that the invention is not limited to the precise embodiments shown.

In the drawings.

DETAILED DESCRIPTION

Figure 1:
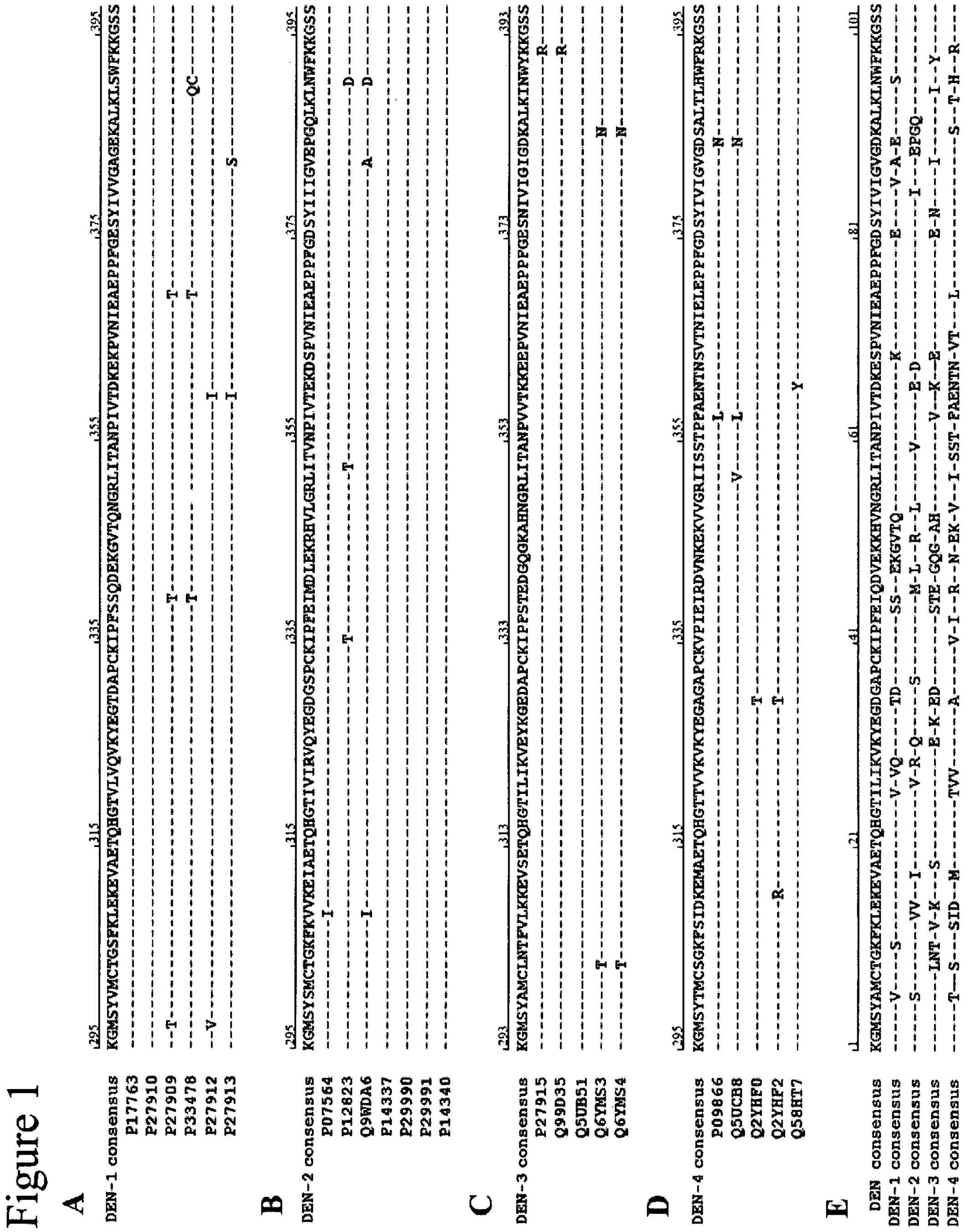
FIG. 1 illustrates the design of a peptide vaccine for four serotypes of dengue viruses according to embodiments of the present invention. Consensus sequences for domain III of envelope proteins (E3) from each serotype of dengue virus were determined by aligning the amino acid sequences of different isolates of each serotype, represented by the Genbank® accession numbers as shown: (A) DEN-1 consensus (SEQ ID NO:1), P17763 (SEQ ID NO:1), P27910 (SEQ ID NO:1), P27909 (SEQ ID NO:7), P33478 (SEQ ID NO:8), P27912 (SEQ ID NO:9), and P27913 (SEQ ID NO:10); (B) DEN-2 consensus (SEQ ID NO:2), P07564 (SEQ ID NO:11), P12823 (SEQ ID NO:12), Q9WDA6 (SEQ ID NO:13), P14337 (SEQ ID NO:2), P29990 (SEQ ID NO:2), P29991 (SEQ ID NO:2), and P14340 (SEQ ID NO:2); (C) DEN-3 consensus (SEQ ID NO:3), P27915 (SEQ ID NO:14), Q99D35 (SEQ ID NO:14), Q5UB51 (SEQ ID NO:3), Q6YMS3 (SEQ ID NO:15), and Q6YMS4 (SEQ ID NO:15); (D) DEN-4 consensus (SEQ ID NO:4), P09866 (SEQ ID NO:16), Q5UCB8 (SEQ ID NO:17), Q2YHF0 (SEQ ID NO:18), Q2YHF2 (SEQ ID NO:19), and Q58HT7 (SEQ ID NO:20); (E) DEN consensus (SEQ ID NO:5), DEN-1 consensus (SEQ ID NO:1), DEN-2 consensus (SEQ ID NO:2), DEN-3 consensus (SEQ ID NO:3), and DEN-4 consensus (SEQ ID NO:4).

Various publications, articles and patents are cited or described in the background and throughout the specification; each of these references is herein incorporated by reference in its entirety. Discussion of documents, acts, materials, devices, articles or the like which has been included in the present specification is for the purpose of providing context for the present invention. Such discussion is not an admission that any or all of these matters form part of the prior art with respect to any inventions disclosed or claimed herein.

DEFINITIONS

Unless defined otherwise, all technical and scientific terms used herein have the same meaning as commonly understood to one of ordinary skill in the art to which this invention pertains. In this application, certain terms are used frequently, which shall have the meanings as set forth in the specification. It must be noted that as used herein and in the appended claims, the singular forms “a,” “an,” and “the” include plural referents unless the context clearly dictates otherwise.

An “adjuvant” as used herein refers to a substance added to an immunogenic composition, such as a vaccine, that while not having any specific antigenic effect in itself, can stimulate the immune system and increase the immune response to the immunogenic composition. Examples of adjuvants include, but are not limited to, alum-precipitate, Freund’s complete adjuvant, Freund’s incomplete adjuvant, monophosphoryl-lipid A/trehalose dicorynomycolate adjuvant, water in oil emulsion containing *Corynebacterium parvum* and tRNA, and other substances that accomplish the task of increasing immune response by mimicking specific sets of evolutionarily conserved molecules including liposomes, lipopolysaccharide (LPS), molecular cages for antigen, components of bacterial cell walls, and endocytosed nucleic acids such as double-stranded RNA, single-stranded DNA, and unmethylated CpG dinucleotide-containing DNA.

An “antibody” as used herein refers to an immunoglobulin molecule or at least one immunologically active portion of an immunoglobulin molecule that has a specific amino acid sequence and binds only to an antigen or a group of antigens that are closely related. Examples of “antibodies” include IgG, IgM, IgA, IgD and IgE. Examples of immunologically active portions of immunoglobulin molecules include Fab and $F(ab)'_2$ fragments which can be generated by treating the antibody with an enzyme such as pepsin. Examples of antibodies includes antivenin (or antivenom, or antivenene), a biological product that is used in the treatment of venomous bites or stings. An “antibody” can be a monoclonal antibody or a polyclonal antibody. The term “monoclonal antibody” refers to a population of antibody molecules that contains only one species of an antigen binding site and that is capable of immunoreacting with a particular epitope. The term “polyclonal antibody” refers to a population of antibody molecules that contains more than one species of antigen binding sites and that is capable of immunoreacting with more than one epitope on the polypeptide.

An “antigen” as used herein refers to a molecule containing one or more epitopes that will stimulate a host’s immune system to make a humoral and/or cellular antigen-specific response. The term “antigen” is used herein interchangeably with “immunogen.” As a result of coming in contact with appropriate cells, an “antigen” induces a state of sensitivity or immune responsiveness and reacts in a demonstrable way with antibodies or immune cells of the sensitized subject in vivo or in vitro. An "antigen" can be specifically recognized and bound by antibodies in an organism. An antigen in association with a major histocompatibility complex (MHC) can also be recognized and bound by receptors on the surface of T lymphocytes (T-cells), leading to the activation of the T-cells.

The term "biological sample" refers to a sample obtained from an organism (e.g., patient) or from components (e.g., cells) of an organism. The sample may be of any biological tissue, cell(s) or fluid. The sample may be a "clinical sample" which is a sample derived from a subject, such as a human patient or veterinary subject. Such samples include, but are not limited to, saliva, sputum, blood, blood cells (e.g., white cells), amniotic fluid, plasma, semen, bone marrow, and tissue or fine needle biopsy samples, urine, peritoneal fluid, and pleural fluid, or cells therefrom. Biological samples may also include sections of tissues such as frozen sections taken for histological purposes. A biological sample may also be referred to as a "patient sample." A "biological sample" may also include a substantially purified or isolated protein, membrane preparation, or cell culture.

The term "consensus sequence" as used herein refers to an amino acid or nucleic acid sequence that is determined by aligning a series of multiple sequences and that defines an idealized sequence that represents the predominant choice of amino acid or base at each corresponding position of the multiple sequences. Depending on the sequences of the series of multiple sequences, the consensus sequence for the series can differ from each of the sequences by zero, one, a few, or more substitutions. Also, depending on the sequences of the series of multiple sequences, more than one consensus sequence may be determined for the series. The generation of consensus sequences has been subjected to intensive mathematical analysis. Various software programs can be used to determine a consensus sequence.

The term "dengue virus" or "DEN" refers to a virus of the genus *Flavivirus* and family Flaviviridae, which is the etiologic agent of dengue diseases or disorders in humans, monkeys, chimpanzees, and other animals, especially mammals. The term "dengue virus" includes any dengue virus of the four currently recognized serotypes, dengue-1, dengue-2, dengue-3, and dengue-4.

The term "dengue disease or disorder" as used herein refers to a disease or disorder caused by the infection of a dengue virus, that is transmitted by an infected mosquito. The infected mosquito can be the *Aedes aegypti* (rarely *Aedes albopictus*) mosquito. The term "dengue disease or disorder" includes dengue fever (DF), dengue hemorrhagic fever (DHF), dengue shock syndrome (DSS), and any other diseases or disorders caused by the infection of a dengue virus.

The term "effective amount" as used herein, means that amount of a composition that elicits a biological or medicinal response in a tissue system of a subject, or in a subject, that is being sought by a researcher, veterinarian, medical doctor or other clinician.

In an embodiment of the invention, the biological or medicinal response includes an immunogenic response induced by a composition comprising an immunogenic composition according to embodiments of the invention. One skilled in the art will recognize that such "immunogenically effective amount" depends on factors, such as the particular subject, e.g., age, weight, diet, health, prior infection history, the particular immunogenic composition used, etc. Standard procedures can be performed to evaluate the immunogenic effect of the administration of an immunogenic composition to a subject, thus allowing a skilled artisan to determine the immunogenically effective amount of the immunogenic composition according to embodiments of the invention to be administered to the subject in view of the present disclosure.

In another embodiment of the invention, the biological or medicinal response includes a clinically observable beneficial effect resulting from the vaccination with a vaccine according to embodiments of the invention. One skilled in the art will recognize that such "vaccination effective amount" depends on factors, such as the particular subject, e.g., age, weight, diet, health, prior infection history, the particular vaccine used, the times of repeated vaccination, etc. Standard procedures can be performed to evaluate the vaccination effect of the administration of a vaccine to a subject, thus allowing a skilled artisan to determine the vaccination effective amount of the vaccine according to embodiments of the invention to be administered to the subject in view of the present disclosure.

In yet another embodiment of the invention, the biological or medicinal response includes a clinically observable beneficial effect resulting from the treatment of a dengue disease or disorder with a therapeutic composition comprising an antibody that selectively binds to a peptide consisting essentially of SEQ ID NO:5. According to one specific example of the present invention, the peptide may be SEQ ID NO:6. In one embodiment of the invention, a "therapeutically effective amount" of a composition according to embodiments of the invention abolishes an existing dengue disease or disorder. In another embodiment of the invention, a "therapeutically effective amount" of a composition according to embodiments of the invention reduces a dengue disease or disorder before or after the occurrence of the disease or disorder to a degree that is less than about 10%, 20%, 30%, 40%, 50%, 60%, 70%, 80%, or 90% or more of what would have been observed when the subject has not received a therapeutically effective amount of the composition. Standard procedures can be performed to evaluate the therapeutic effect of the administration of a vaccine to a subject, thus allowing a skilled artisan to determine the therapeutically effective amount of the composition according to embodiments of the invention to be administered to the subject in view of the present disclosure.

The term "epitope" as used herein refers to the site on an antigen to which a specific antibody molecule or a T-cell receptor binds. The term "epitope" is used herein interchangeably with "antigenic determinant" or "antigenic determinant site."

The term "immune response" or "immunogenic response" as used herein refers to any reaction of the immune system in response to an antigen in a subject. Examples of an immune response in a vertebrate include, but are not limited to, antibody production, induction of cell-mediated immunity, complement activation, and development of immune tolerance. The immune response to a subsequent stimulus by the same antigen, also named the secondary immune response, is more rapid than in the case of the primary immune response.

An isolated, recombinant or synthetic peptide of the present invention is "substantially purified" in that the peptide is substantially free of cellular material or other contaminating peptides or proteins from the cell or tissue source from which the peptide is derived, or substantially free of chemical precursors or other chemicals when chemically synthesized. Preparations of peptide substantially free of cellular material include those in which the peptide is separated from cellular components of the cells from which it is isolated or recombinantly produced. Thus, peptide that is substantially free of cellular material includes preparations of peptide having less than about 30%, 20%, 10%, or 5% (by weight) of heterologous protein or peptide (also referred to herein as a "contaminating protein or peptide"). When the peptide is recombinantly produced, it is also preferably substantially free of culture medium, i.e., culture medium represents less than about 20%, 10%, or 5% of the volume of the peptide preparation. When the peptide is produced by chemical synthesis, it is preferably substantially free of chemical precursors or other chemicals, i.e., it is separated from chemical precursors or other chemicals that are involved in the synthesis of the peptide. Accordingly, such preparations of peptide have less than about 30%, 20%, 10%, 5% (by weight) of chemical precursors or compounds other than the peptide of interest. Especially, but not exclusively, when a preparation of isolated, recombinant or synthetic peptide is used for administration to a subject for vaccination or other pharmaceutical purposes, the preparation may contain contaminating peptides or proteins, other cellular materials, or other chemicals only in such amounts that do not have a biologically adverse effect on the subject.

The isolated, recombinant or synthetic peptide can have several different physical forms. Such a peptide can exist as a full-length nascent or unprocessed peptide, as a partially processed peptide, or as a combination of processed peptides. The full-length nascent peptide can be postranslationally modified by specific proteolytic cleavage events that result in the formation of fragments of the full-length nascent peptide. The peptide can be encoded by an isolated nucleic acid sequence or synthesized by, for example, chemical synthetic methods. The peptide can be separated from biological materials, chemical precursors, or other chemicals and then isolated, using conventional protein analytical or preparatory procedures, to an extent that permits it to be used according to the methods described herein.

As used herein, the term "neutralization" when used in the context of antibody responses refers to the ability of an antibody to bind to a site on a dengue virus to block docking or binding of the dengue virus to a host cell, thus preventing infection of the host cell by the dengue virus. The dengue virus uses the site to dock or bind itself to a receptor on the host cell in order to infect the host cell. The term "cross-neutralization" as used herein, refers to the ability of an antibody to bind to multiple serotypes of dengue viruses to block docking or binding of the viruses to a host cell, thus preventing infection of the host cell by the multiple serotypes of dengue viruses.

The term "peptide antigen" as used herein refers to an antigen that is made of a peptide. A "peptide antigen" contains one or more epitopes, each formed by a specified amino acid sequence. The peptide antigen may include amino acid substitutions which preserve the immunogenic specificity of the antigen.

A "peptide" refers to the arrangement of amino acid residues in a polymer. A peptide can be composed of the standard 20 naturally occurring amino acid, in addition to rare amino acids and synthetic amino acid analogs. A "recombinant peptide" refers to a peptide produced by recombinant DNA techniques; i.e., produced from cells transformed by an exogenous DNA construct encoding the desired peptide. A "synthetic peptide" refers to a peptide prepared by chemical synthesis.

As used herein, the term "subject" refers to an animal, preferably a mammal, who has been the object of diagnosis, treatment, observation or experiment. Examples of a subject can be a human, a livestock animal (beef and dairy cattle, sheep, poultry, swine, etc.), or a companion animal (dogs, cats, horses, etc).

As used herein, the term "treating a dengue disease or disorder" or "treatment of a dengue disease or disorder" means to interdict, palliate, alleviate, reduce, decrease, or prevent the dengue disease or disorder. "Treating a dengue disease or disorder" includes both therapeutic treatment of an existing dengue disease or disorder and prophylactic treatment before symptoms of a dengue disease or disorder are developed or observable. "Treating a dengue disease or disorder" results in a clinically observable beneficial effect. The clinically observable beneficial effect includes a therapeutic treatment situation where a composition of an embodiment of the present invention is administered to a subject after symptoms of existing a dengue disease or disorder are observable, and the observable symptoms of the existing disease or disorder are either abolished or reduced to a lesser degree than without the treatment. The clinically observable beneficial effect also includes a prophylactic treatment situation where a composition of an embodiment of the present invention is administered to a subject before symptoms of dengue disease or disorder are observable, and symptoms of a dengue disease or disorder are prevented from occurring or symptoms of a dengue disease or disorder subsequently occur, but to a lesser degree than without administration of the composition.

The term "vaccine" as used herein refers to any preparation intended for administration to a subject to produce or artificially increase immune response to a particular disease in the subject. Examples of vaccines include preparations of killed, often virulent strains of, infectious agents including, but not limited to, a microorganism (a bacterium, virus, etc.), fungus, protozoan, metazoan, or plant. Examples of vaccines also include preparations of living, often attenuated (variant or mutant) strains of, infectious agents. Examples of vaccines further include preparations of sub-parts, portions, or products of infectious agents, such as a peptide antigen from an infectious agent.

There are three structural proteins present in a mature dengue virion: a core nucleocapsid protein (C), a transmembrane protein (M), and a major envelope glycoprotein (E). Crystallographic studies of E protein from dengue virus and other flaviviruses have revealed that it contains three domains (I-III) (Modis et al., 2003, *PNAS* 100:6986-6991; Modis et al., 2005, *J. Virol.* 79:1223-1231; Rey et al., *Nature* 375:291-298). Domain III of the E protein has an IgG-like fold and determinants that participate in most of the relevant biological events including virulence and/or neurovirulence (Cecilia et al., 1991, *Virology* 181:70-77; Leitmeyer et al., 1999, *J. Virol.* 73:4738-4747; Lobigs et al., 1990, *Virology* 176:587-595; Pletnev et al., 1993, *J. Virol.* 67:4956-4963; Sanchez et al., 1996, *J Gen Virol* 77:2541-2545; Sumiyoshi et al., 1995. *J Infect Dis* 171:1144-1151.). Domain III is also involved in binding host receptors (Chen et al., 1997, *Nat Med* 3:866-871; and Hung et al., 2004, *J. Virol.* 78:378-3883) and it contains type and subtype-specific epitopes that elicit only neutralizing antibodies (Crill et al., 2001, *J. Virol.* 75:7769-7773; Hiramatsu et al., 1996, *Virology* 224:437-445; Roehrig, et al., 1998, *Virology* 246:317-328; Roehrig et al., 1994, *Virology* 198:31-38; Thullier et al., 2001, *J Gen Virol* 82:1885-1892; Trirawatanapong et al., 1992. *Gene* 116:139-150). Even though domain III of the envelope protein (E3) represents only a fraction of the envelope protein, the absence of other epitopes which elicit non-neutralizing, cross-reactive antibodies would have advantages in reducing risk for progression to DHF or DSS. It has been demonstrated that immunization with DNA encoding E3 elicited protective antibodies against dengue virus in a mouse model (Mota et al., 2005, *Vaccine* 23:3469-3476). These results suggest that E3 is a potential subunit vaccine candidate.

A consensus peptide from E3 of four serotypes of dengue virus was designed in accordance with the present invention. Such consensus peptide was able to elicit cross-neutralization antibody responses against multiple serotypes of dengue viruses.

In one embodiment, the invention relates to an isolated, recombinant or synthetic peptide consisting essentially of SEQ ID NO:5. SEQ ID NO:5 is a consensus peptide sequence designed by sequence analysis of E3 from the four serotypes of dengue viruses. According to one specific example, the synthetic peptide may consist essentially of SEQ ID NO:6. SEQ ID NO: 6 is a synthetic peptide sequence derived from position 7 to 40 of SEQ ID NO:5. A peptide consisting either of SEQ ID NO:5 or SEQ ID NO: 6 may be used as a peptide antigen to elicit immune response against one or more, and preferably all four, serotypes of dengue viruses.

A peptide consisting essentially of SEQ ID NO: 5 can be produced by various means. For example, the peptide can be produced by recombinant DNA techniques or from an in vitro translation system, or can be synthesized chemically using standard peptide synthesis techniques. In a preferred embodiment, the peptide is produced by chemical synthesis, such as solid phase peptide synthesis on an automated peptide synthesizer. Such methods are known to those skilled in the art and could be readily adapted to the present invention in view of the present disclosure.

A peptide consisting essentially of SEQ ID NO: 5 can be substantially purified by methods known to those skilled in the art in view of the present disclosure. For example, the peptide can be substantially purified from cell lysates and extracts, or from the reaction mixture of chemical synthesis by various combinations of, or individual application of salt fractionation, ion exchange chromatography, size exclusion chromatography, hydroxylapatite adsorption chromatography and hydrophobic interaction chromatography, lectin chromatography, HPLC, and FPLC, and antibody/ligand affinity chromatography.

In another embodiment, the invention relates to an immunogenic composition comprising a peptide consisting essentially of SEQ ID NO:5. The immunogenic composition comprises the peptide consisting essentially of SEQ ID NO:5 in an amount that is effective to induce an immune response when the immunogenic composition is administered to a subject. In some embodiments, the immunogenic composition comprises about 0.5 microgram (μg) to about 1 milligram (mg) of a peptide consisting essentially of SEQ ID NO:5 per dose of administration. For example, an immunogenic composition according to embodiments of the invention can comprise about 0.5 μg to about 10 μg, about 10 μg to about 100 μg, about 100 μg to about 500 μg, or about 500 μg to about 1000 μg, of a peptide consisting essentially of SEQ ID NO:5 per dose of administration.

In addition to the peptide consisting essentially of SEQ ID NO:5, the immunogenic composition also comprises other ingredients, such as a physiologically acceptable vehicle and/or adjuvant. Such vehicles and/or adjuvants are well known in the art. The vehicles may include, but are not limited to, water, buffered water, saline solution, glycine solution, hyaluronic acid and the like, pH adjusting and buffering agents, tonically adjusting agents, and wetting agents. Non-limiting examples of adjuvants that can be used in the present invention are described above.

In another embodiment, the invention relates to a kit comprising an immunogenic composition according to embodiments of the invention and instructions for using the immunogenic composition to induce an immune response in a subject. For example, the kit can be a container, such as a bottle, a jar, or a box, containing the composition, with the instructions accompanying, or contained in or on the container, such as affixed or imprinted onto a surface or a label of the container.

Another embodiment of the present invention also includes a method of inducing an immune response in a subject. The method comprises administering to the subject an immunogenically effective amount of an immunogenic composition according to any of the embodiments of the invention. The immunogenic composition can be administered to a subject by various means, such as ingestion, nasal spray, subcutaneous (SC) injection, intraperitoneal (IP) injection, intravenous infusion, intravenous injection, intramuscular injection, transdermal patch, or combinations thereof. The immune response comprises neutralization antibody responses against one or more serotypes of dengue viruses. Preferably, the immune response comprises cross-neutralization antibody responses against all four serotypes of dengue viruses.

In particular embodiments of the invention, the immunogenic composition is a vaccine to be used against one or more dengue viruses selected from the group consisting of serotypes 1-4 dengue viruses. The vaccine can be used to prevent a dengue disease or disorder in a subject. In one embodiment, the vaccine is used to prevent a serious or life-threatening dengue disease such as DHF or DSS. A vaccination effective amount of the vaccine according to embodiments of the invention can be administered to a subject in a single administration or multiple administrations. Multiple administrations of the vaccine may be required to elicit sufficient levels of immunity. Levels of induced immunity can be monitored by measuring the amount of neutralizing antibodies in biological samples from the subject. The vaccination dosage and times can be adjusted as necessary to maintain desired levels of protection.

In some embodiments of the present invention, a vaccine according to embodiments of this invention will be administered either singly or concomitantly with one or more other vaccines that induce protective responses against one or more other infectious agents or against one or more serotypes of dengue viruses by other mechanisms of action. The concomitant administration can involve concurrent (i.e. at the same time), prior, or subsequent administration of the other vaccine (s) with respect to the administration of a vaccine according to embodiments of the present invention. A person of ordinary skill in the art would have no difficulty determining the appropriate timing, sequence and dosages of administration for particular vaccines in view of the present disclosure.

Another general aspect of the invention relates to a substantially purified antibody that selectively binds to a peptide consisting essentially of SEQ ID NO:5. The antibody according to embodiments of the invention binds specifically to an envelope protein of one or more serotypes of dengue viruses. The antibody binds specifically to a domain III region of the envelope protein, more particularly, a sequence within the domain III region that is substantially similar to SEQ ID NO:5.

An antibody according to embodiments of the invention can be produced by various methods. In one embodiment, polyclonal antibodies can be raised by immunizing suitable subject animals such as mice, rats, guinea pigs, rabbits, goats, horses and the like, with rabbits being preferred, with the immunogen of embodiments of the invention, with or without an immune adjuvant. Pre-immune serum is collected prior to the first immunization. Each animal receives between about 0.001 mg and about 1000 mg of the immunogen associated with or without an acceptable immune adjuvant. The initial immunization can be with a peptide consisting essentially of SEQ ID NO:5 in, preferably, Freund's complete adjuvant administered at multiple sites either subcutaneously (SC), intraperitoneally (IP) or both. Each animal is bled at regular intervals, preferably weekly, to determine antibody titer. The animals may or may not receive booster injections following the initial immunization. Those animals receiving booster injections are generally given an equal amount of the antigen in Freund's incomplete adjuvant by the same route. Booster injections are given at about three-week intervals until maximal titers are obtained. At about 7 days after each booster immunization or about weekly after a single immunization, the animals are bled, the serum collected, and aliquots are stored at about −20° C.

In another embodiment, monoclonal antibodies (mAbs) may be prepared by immunizing inbred mice, preferably Balb/c, with the immunogen of the invention. The mice are immunized by the IP or SC route with about 0.001 mg to about 1.0 mg, preferably about 0.1 mg, of the immunogen in about 0.1 ml buffer or saline incorporated in an equal volume of an acceptable adjuvant, as discussed above. Freund's adjuvant is preferred, with Freund's complete adjuvant being used for the initial immunization and Freund's incomplete adjuvant used thereafter. The mice receive an initial immunization on day 0 and are rested for about 2 to about 30 weeks. Immunized mice are given one or more booster immunizations of about 0.001 mg to about 1.0 mg of a peptide consisting essentially of SEQ ID NO:5 in a buffer solution such as phosphate buffered saline by the intravenous (IV) route.

Lymphocytes, from antibody positive mice, preferably spleenic lymphocytes, are obtained by removing spleens from immunized mice by standard procedures known in the art. Hybridoma cells are produced by mixing the splenic lymphocytes with an appropriate fusion partner, preferably myeloma cells, under conditions that will allow the formation of stable hybridomas. Fusion partners may include, but are not limited to: mouse myelomas P3/NS1/Ag 4-1; MPC-11; S-194 and Sp2/0, with Sp2/0 being generally preferred. The antibody producing cells and myeloma cells are fused in polyethylene glycol, about 1000 mol. wt., at concentrations of about 30% to about 50%. Fused hybridoma cells are selected by growth in hypoxanthine, thymidine and aminopterin supplemented Dulbecco's Modified Eagles Medium (DMEM) by procedures known in the art in view of the present disclosure. Supernatant fluids are collected from growth positive wells on about days 14, 18, and 21 and are screened for antibody production by an immunoassay such as solid phase immunoradioassay (SPIRA) using a peptide consisting essentially of SEQ ID NO:5 as the antigen. The culture fluids are also tested in the Ouchterlony precipitation assay to determine the isotype of the mAb.

Hybridoma cells from antibody positive wells are cloned by a technique such as the soft agar technique of MacPherson, Soft Agar Techniques, in Tissue Culture Methods and Applications, Kruse and Paterson, Eds., Academic Press, 1973 or by the technique of limited dilution. Monoclonal antibodies are produced in vivo by injection of pristane primed Balb/c mice, approximately 0.5 ml per mouse, with about $1\times10^6$ to about $6\times10^6$ hybridoma cells at least about 4 days after priming. Ascites fluid is collected at approximately 8-12 days after cell transfer and the monoclonal antibodies are purified by techniques known in the art. Monoclonal antibodies can also be produced in vitro by growing the hydridoma in tissue culture media well known in the art in view of the present disclosure. High density in vitro cell culture can be conducted to produce large quantities of mAbs using hollow fiber culture techniques, air lift reactors, roller bottle, or spinner flasks culture techniques well known in the art. The mAbs are purified by techniques known in the art in view of the present disclosure.

Titers of a preparation containing an antibody according to embodiments of the invention can be determined by various serological or immunological assays. Such assays include, but are not limited to, precipitation, passive agglutination, enzyme-linked immunosorbent antibody (ELISA) technique and radioimmunoassay (RIA) techniques.

An antibody according to embodiments of the invention can be isolated from a mammal (e.g., from the blood) or culture cells and further purified by well-known techniques in view of the present disclosure. For example, protein A chromatography can be used to obtain the IgG fraction. Alternatively, antibodies specific for a peptide of the invention can be selected for (e.g., partially purified) or purified by, e.g., affinity chromatography. For example, an isolated or substantially purified peptide consisting essentially of SEQ ID NO:5 is produced as described herein, and covalently or non-covalently coupled to a solid support such as, for example, a chromatography column. The column can then be used to affinity purify antibodies specific for the peptide according to embodiments of the invention from a sample containing antibodies directed against a large number of different epitopes, thereby generating a substantially purified antibody composition, i.e., one that is substantially free of contaminating antibodies.

Additionally, recombinant antibodies, such as chimeric and humanized monoclonal antibodies, comprising both human and non-human portions, which can be made using standard recombinant DNA techniques, are within the scope of the invention. A chimeric antibody is a molecule in which different portions are derived from different animal species, such as those having a variable region derived from a murine mAb—and a human immunoglobulin constant region. Humanized antibodies are antibody molecules from non-human species having one or more complementarily determining regions (CDRs) from the non-human species and a framework region from a human immunoglobulin molecule. Such chimeric and humanized monoclonal antibodies can be produced by recombinant DNA techniques known in the art.

Completely human antibodies are particularly desirable for therapeutic treatment of human patients. Such antibodies can be produced, for example, using transgenic mice which are incapable of expressing endogenous immunoglobulin heavy and light chains genes, but which can express human heavy and light chain genes. The transgenic mice are immunized in the normal fashion with a selected antigen, e.g., all or a portion of a peptide of the invention. Monoclonal antibodies directed against the antigen can be obtained using conventional hybridoma technology. The human immunoglobulin transgenes harbored by the transgenic mice rearrange during B cell differentiation, and subsequently undergo class switching and somatic mutation. Thus, using such a technique, it is possible to produce therapeutically useful IgG, IgA and IgE antibodies.

Completely human antibodies which recognize a selected epitope can be generated using a technique referred to as "guided selection." In this approach a selected non-human monoclonal antibody, e.g., a mouse antibody, is used to guide the selection of a completely human antibody recognizing the same epitope.

The antibody that selectively binds to a peptide consisting essentially of SEQ ID NO:5 can be used diagnostically to detect the presence of an envelope protein of a dengue virus, and thus the dengue virus, in a subject as part of a clinical testing procedure. Therefore, in one embodiment, the invention also relates to a method of detecting dengue virus infection in a subject, comprising: (a) obtaining a biological sample from the subject; (b) contacting the biological sample with an antibody that selectively binds to a peptide consisting essentially of SEQ ID NO:5; and (c) detecting the presence of an antigen in the biological sample that binds specifically to the antibody. In a preferred embodiment, the biological sample is a blood sample, more preferably a serum sample, which is obtained from the subject via any conventional means.

The detection of the presence of an antigen can be performed by various immunological assays, such as precipitation, passive agglutination, enzyme-linked immunosorbent antibody (ELISA) technique and radioimmunoassay (RIA) techniques. The detection assay can be facilitated by coupling the antibody to a detectable substance. Examples of detectable substances include various enzymes, prosthetic groups, fluorescent materials, luminescent materials, bioluminescent materials, and radioactive materials. Examples of suitable enzymes include horseradish peroxidase, alkaline phosphatase, beta-galactosidase, or acetyleholinesterase. Examples of suitable prosthetic group complexes include streptavidin/biotin and avidin/biotin. Examples of suitable fluorescent materials include umbelliferone, fluorescein, fluorescein isothiocyanate, rhodamine, dichlorotriazinylamine fluorescein, dansyl chloride or phycoerythrin. An example of a luminescent material includes luminol. Examples of bioluminescent materials include luciferase, luciferin, and aequorin. Examples of suitable radioactive material include $^{125}I$, $^{131}I$, $^{35}S$ or $^{3}H$.

In another embodiment, the invention relates to a kit for detecting dengue virus infection in a subject. The kit comprises an antibody that selectively binds to a peptide consisting essentially of SEQ ID NO:5 and instructions for using the antibody to detect a dengue infection in the subject. The kit can be a container, such as a bottle, a jar, or a box, containing the composition, with the instructions accompanying, or contained in or on the container, such as affixed or imprinted onto a surface or a label of the container. The kit can further include a preparation containing a peptide consisting essentially of SEQ ID NO:5 as a positive control.

Another method of detecting dengue virus infection in a subject involves detecting the presence of an antibody in a biological sample of the subject that binds specifically to an antigen according to embodiments of the invention. The diagnostic method comprises: (a) obtaining a biological sample from the subject; (b) contacting the biological sample with a peptide consisting essentially of SEQ ID NO:5; and (c) detecting the presence of an antibody in the biological sample that binds specifically to the peptide. In a preferred embodiment, the biological sample is a blood sample, more preferably a serum sample, which is obtained from the subject via any conventional means.

Various immunological assays as described above can be used in the detection assay. Similarly, the peptide consisting essentially of SEQ ID NO:5 can be coupled to a detectable substance to facilitate the detection.

In another embodiment, the invention relates to a kit for detecting a dengue virus infection in a subject, comprising a peptide consisting essentially of SEQ ID NO:5 and instructions for using the peptide to detect a dengue infection in the subject. The kit can be a container, such as a bottle, a jar, or a box, containing the composition, with the instructions accompanying, or contained in or on the container, such as affixed or imprinted onto a surface or a label of the container. The kit can further include a preparation containing an antibody that selectively binds to a peptide consisting essentially of SEQ ID NO:5 as a positive control.

Further, an antibody (or fragment thereof) according to embodiments of the invention can be used to treat a dengue infection. Previous study demonstrates that monoclonal antibodies that bind to E3 are the most efficient blockers of virus adsorption to Vero cells. A peptide consisting essentially of SEQ ID NO:5 is a consensus sequence for E3 from the four serotypes of dengue viruses. Antibodies that bind specifically to the peptide are capable of binding specifically to E3 from the four serotypes of dengue viruses. Therefore, such antibodies can be used to cross-neutralize and block infections by multiple serotypes of dengue viruses.

An embodiment of the present invention relates to a therapeutic composition comprising an antibody that selectively binds to a peptide consisting essentially of SEQ ID NO:5 and a pharmaceutically acceptable vehicle. The therapeutic composition according to embodiments of the present invention can be formulated according to known methods for preparing pharmaceutically useful compositions in view of the present disclosure. Sterile phosphate-buffered saline is one example of a pharmaceutically acceptable vehicle. Other acceptable vehicles are well-known to those in the art and could be used in view of the present disclosure.

Formulations of the antibody according to embodiments of the present invention can be presented in unit dosage form, e.g., in multi-dose containers, with an added preservative. The compositions can take such forms as suspensions, solutions or emulsions in oily or aqueous vehicles, and can contain formulatory agents such as suspending, stabilizing and/or dispersing agents. Alternatively, the active ingredient can be in powder form for constitution with a suitable vehicle, e.g., sterile pyrogen-free water, before use.

Another embodiment of the present invention relates to a method of treating a dengue disease or disorder in a subject, comprising administering to the subject a therapeutically effective amount of a therapeutic composition according to embodiments of the invention. In one embodiment, the therapeutic composition according to embodiments of the invention can be administered to a subject by intravenous administration via, for example, bolus injection or continuous infusion. In some embodiments, an antibody according to embodiments of this invention will be administered either singly or concomitantly with at least one or more other therapeutic agents. The concomitant administration can involve concurrent (i.e. at the same time), prior, or subsequent administration of the other therapeutic agent(s) with respect to the administration of an antibody according to embodiments of the present invention. A person of ordinary skill in the art would have no difficulty determining the appropriate timing, sequence and dosages of administration for particular vaccines in view of the present disclosure.

A further embodiment of the present invention relates to a method of designing a peptide vaccine against one or more dengue viruses selected from the group consisting of serotypes 1, 2, 3, and 4 dengue viruses. As illustrated in Example 1 below, the method comprises: (a) determining a consensus sequence for the amino acid sequences of E3 from the one or more dengue viruses selected from the group consisting of serotypes 1, 2, 3, and 4 dengue viruses; and (b) designing the peptide vaccine comprising a peptide having the consensus sequence.

This invention will be better understood by reference to the specific, non-limiting examples that follow, but those skilled in the art will readily appreciate that the examples are only illustrative of the invention as described more fully in the claims which follow thereafter.

Example 1

Design of a Consensus Sequence for Domain III of E Proteins from Four Serotypes of Dengue Virus A consensus sequence for domain III of envelope proteins (E3) from each serotype of dengue viruses was first determined by aligning sequences from different isolates of the serotype. A consensus sequence for E3 from all four serotypes of dengue virus was then determined by aligning the consensus sequences from dengue-1, dengue-2, dengue-3 and dengue-4 virus, and was used for the design of the peptide vaccine against the four serotypes of dengue virus. The amino acid sequences for E3 can be obtained by various methods known in the art in view of the present disclosure, e.g., from various sequence databases or by sequencing analyses directly.

As illustrated in FIG. 1, amino acid sequences for E3 were first obtained from GenBank® via online access of National Center for Biotechnology Information (NCBI). A consensus sequence for E3 from dengue-1 viruses (DEN-1 consensus, SEQ ID NO:1) was obtained by aligning six amino acid sequences from different isolates of DEN-1 virus (FIG. 1A). The six DEN-1 amino acid sequences have GenBank® accession numbers of P17763 (SEQ ID NO:1), P27910 (SEQ ID NO:1), P27909 (SEQ ID NO:7), P33478 (SEQ ID NO:8), P27912 (SEQ ID NO:9), and P27913 (SEQ ID NO:10), respectively. A consensus sequence for E3 from dengue-2 viruses (DEN-2 consensus, SEQ ID NO:2) was obtained by aligning seven amino acid sequences from different isolates of DEN-2 virus (FIG. 1B). The seven DEN-2 amino acid sequences have GenBank® accession numbers of P07564 (SEQ ID NO:11), P12823 (SEQ ID NO:12), Q9WDA6 (SEQ ID NO:13), P14337 (SEQ ID NO:2), P29990 (SEQ ID NO:2), P29991 (SEQ ID NO:2), and P14340 (SEQ ID NO:2), respectively. A consensus sequence for E3 from dengue-3 viruses (DEN-3 consensus, SEQ ID NO:3) was obtained by aligning five amino acid sequences from different isolates of DEN-3 virus (FIG. 1C). The five DEN-3 amino acid sequences have GenBank® accession numbers of P27915 (SEQ ID NO:14), Q99D35 (SEQ ID NO:14), Q5UB51 (SEQ ID NO:3), Q6YMS3 (SEQ ID NO:15), and Q6YMS4 (SEQ ID NO15), respectively. A consensus sequence for E3 from dengue-4 viruses (DEN-4 consensus, SEQ ID NO:4) was obtained by aligning five amino acid sequences from different isolates of DEN-4 virus (FIG. 1D). The five DEN-4 amino acid sequences have GenBank® accession numbers of P09866 (SEQ ID NO:16), Q5UCB8 (SEQ ID NO:17), Q2YHF0 (SEQ ID NO:18), Q2YHF2 (SEQ ID NO:19), and Q58HT7 (SEQ ID NO:20), respectively. As shown in FIG. 1E, a consensus sequence for E3 from dengue-1, dengue-2, dengue-3, and dengue-4 viruses (DEN consensus, SEQ ID NO:5) was determined by aligning the consensus sequences from each of the four serotypes, DEN-1 consensus (SEQ ID NO:1), DEN-2 consensus (SEQ ID NO:2), DEN-3 consensus (SEQ ID NO:3), and DEN-4 consensus (SEQ ID NO:4).

It is readily appreciated by one skilled in the art that multiple consensus sequences for E3 from dengue-1, dengue-2, dengue-3, and dengue-4 viruses (DEN consensus) can be generated based on the sequence alignment of DEN-1 consensus (SEQ ID NO:1), DEN-2 consensus (SEQ ID NO:2), DEN-3 consensus (SEQ ID NO:3), and DEN-4 consensus (SEQ ID NO:4). For example, position 15 of DEN consensus (SEQ ID NO:5) can be any one of the four amino acids, L-glutamic acid (E), L-valine (V), L-lysine (K), and L-aspartic acid (D); position 27 of SEQ ID NO:5 can be any one of the two amino acids, L-leucine (L) and L-valine (V); position 28 of SEQ ID NO:5 can be any one of the two amino acids, L-isoleucine (I) and L-valine (V); position 35 of SEQ ID NO:5 can be any one of the four amino acids, L-threonine (T), L-aspartic acid (D), L-glutamic acid (E), and L-alanine (A); and position 46 of SEQ ID NO:5 can be any one of the two amino acids, L-glutarmine (Q), L-methionine (M), L-glutamic acid (E), and L-arginine (R). Embodiments of the present invention include such multiple consensus sequences. The following Examples may also apply to other consensus sequences in view of the present disclosure.

Example 2

Preparation of Recombinant DEN Consensus Protein

Figure 2A:
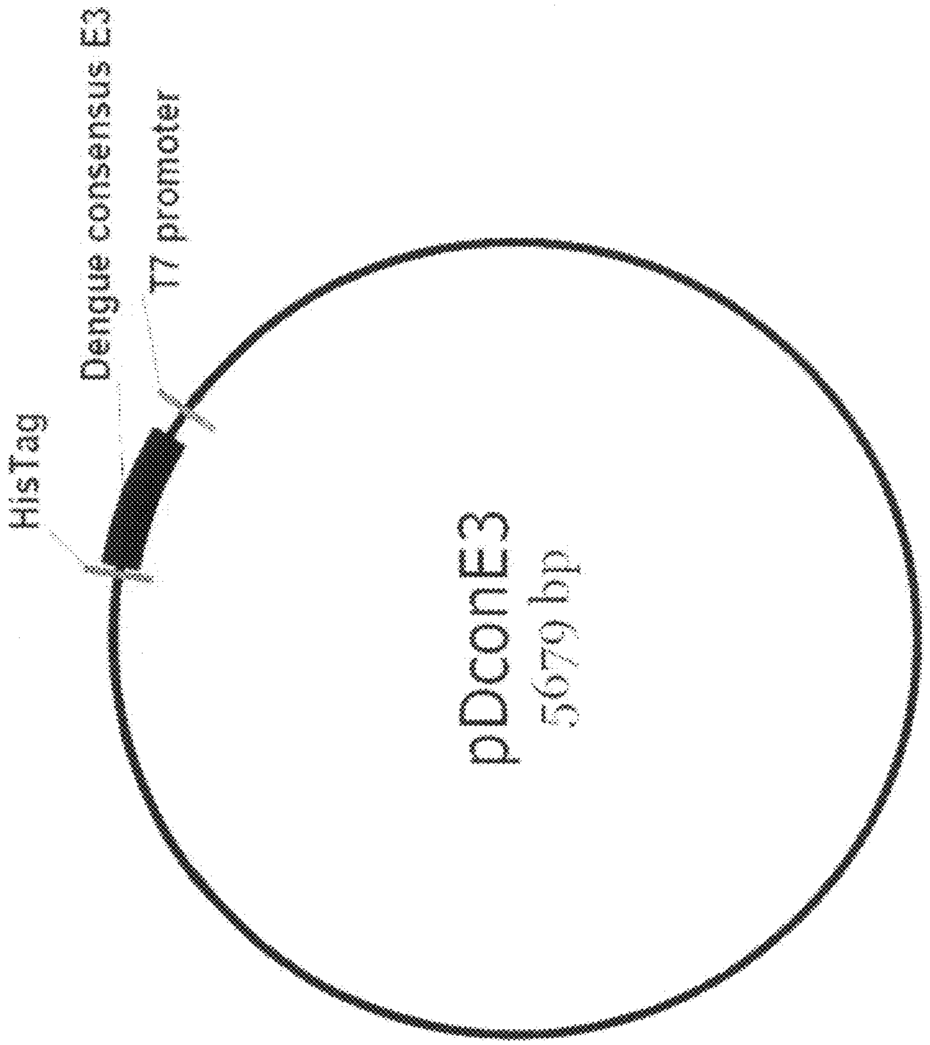
FIG. 2A shows a diagrammatic construct of a plasmid pDconE3 according to embodiments of the present invention.
Figure 2B:
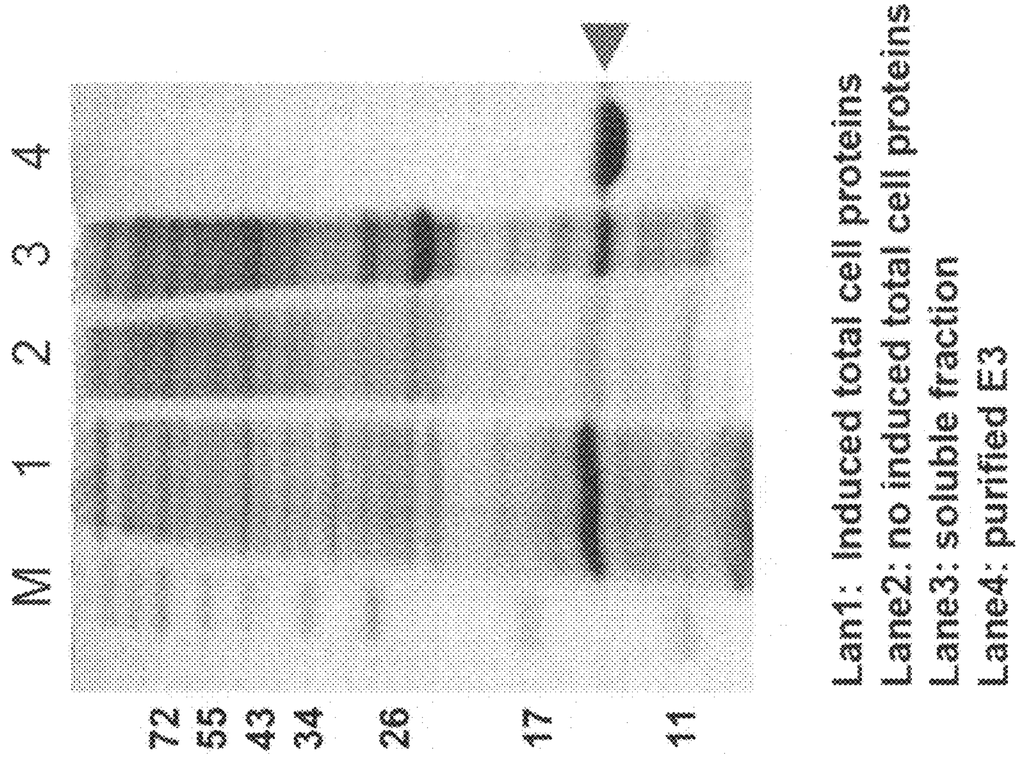
FIG. 2B is a photo of SDS-PAGE gel showing purified E3 protein according to embodiments of the present invention.
Figure 2C:
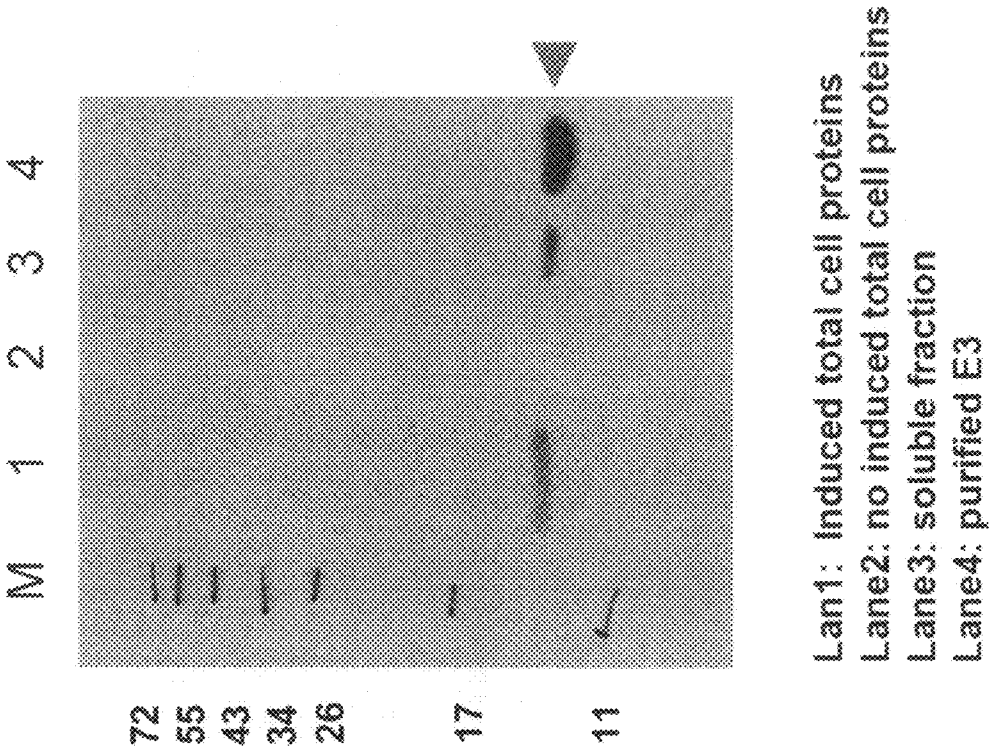
FIG. 2C is an immunoblot showing purified E3 protein according to embodiments of the present invention.

The gene of DEN consensus was obtained by assembly PCR using overlapping primers. The E3 gene was amplified using as template. The forward 5'-ACATATGAAAGGCATGAGCTATGCG-3' primer included a Nde I site and the reverse primer, 5'-ACTCGAGGCTGCTGCCTTTTTTA-3' included a Xho I site. As a result, the C-terminal end of the expressed protein had a hexa-histidine tag. The PCR product was cloned into the expression vector, pET-22b(+) (Novagen, Madison, Wis.) using Nde I and Xho I sites to produce a plasmid pDconE3 as shown in FIG. 2A. The recombinant DEN consensus was expressed in *Escherichia coli* BL21 codon (DE3). After inducing recombinant DEN consensus in BL21 codon(DE3), 2.4 liters of cell culture were spun down (8000×g for 20 min) and the pellets were re-suspended in 100 ml of homogenization buffer (20 mM Tris-Cl (pH 8.0), 500 mM NaCl, 10% glycerol, and 50 mM sucrose). After disruption the cells with a French Press (Constant Systems, Daventry, UK) at 27 Kpsi, The cell lysates were clarified by centrifugation (80,000×g for 60 min). The supernatant was loaded onto a 20 ml Ni-NTA resin (Qiagen, San Diego, Calif., USA). The column (2.2 cm i.d.×5.3 cm) was washed with homogenization buffer and then was further washed with the same buffer containing 40 mM imidazole. The recombinant DEN consensus was then eluted with homogenization buffer containing 500 mM imidazole. The eluted fraction was dialyzed against 20 mM Tris-Cl (pH 8.0) and 1 mM EDTA. The sample was loaded onto a 5 ml Q resin and the flow through was collected. Referring to FIGS. 2B and 2C, the fractions in each step were analyzed using SDS-PAGE and immunoblotting. The purified E3 protein was visible as either a band in the SDS-PAGE gel or immunoblot.

Example 3

Effect of Vaccination with a Vaccine Comprising the Consensus Peptide

Vaccination of mice was performed and the post-vaccination or post-immunization sera were collected following the procedure of Example 2. Pre-vaccination or pre-immunization sera were also collected from the same animals as control. The effect of vaccination was measured from the post-vaccination sera by the neutralization antibody responses against four serotypes of dengue viruses.

BHK cells, cells that have been widely used as viral host cells, were seeded at $2\times10^5$ cells per well in 24-well plates and incubated overnight at 37° C. to produce a confluent monolayer. The cells in the monolayer were inoculated with dengue virus that had been pre-mixed with pre-immunization or post-immunization sera in a final volume of 0.5 mL. The virus titer prior to pre-mixing was about 50 to about 250 focus-forming units (FFU) per well. The pre-mixing was performed for overnight at 4° C. Viral adsorption was allowed to proceed for 2 hours at 37° C., with rocking of the plates every 15 min. An overlay of 0.5×RPMI-1640 medium (Sigma-Aldrich), 2.5% fetal bovine serum (FBS), and 0.5% methyl cellulose was added at the conclusion of adsorption. The infected monolayer was incubated at 37° C. After 72 to 120 hours of infection, the overlay medium was removed from the wells and the BHK cells were washed with cold phosphate buffer saline (PBS). The cells were fixed for 15 min in 3.7% formaldehyde/PBS. After washing with PBS, cells were permeabilized with 0.1% nonidet NP −40/PBS at room temperature for 15 min, and blocked with 3% bovine serum albumin (BSA)/PBS for 30 min. Monoclonal anti-dengue antibody was added to each well, and then incubated at room temperature for 50 min. The monoclonal anti-dengue antibody was derived from the culture supernatant of the hybridoma American Type Culture Collection (ATCC) NO. HB-114. It reacted with all members of the dengue virus. After washing with PBS, antibody-labeled cells were detected by incubation of the cells for 30 min with a secondary antibody conjugated to horseradish peroxidase (HRP). Following washing with PBS, focus-forming units (FFU) were developed by 3,3',5,5'-tetramethylbenzidine (TMB). The FFU were counted, and the neutralization effects of antisera were determined by the reduction of FFU.

Figure 3:
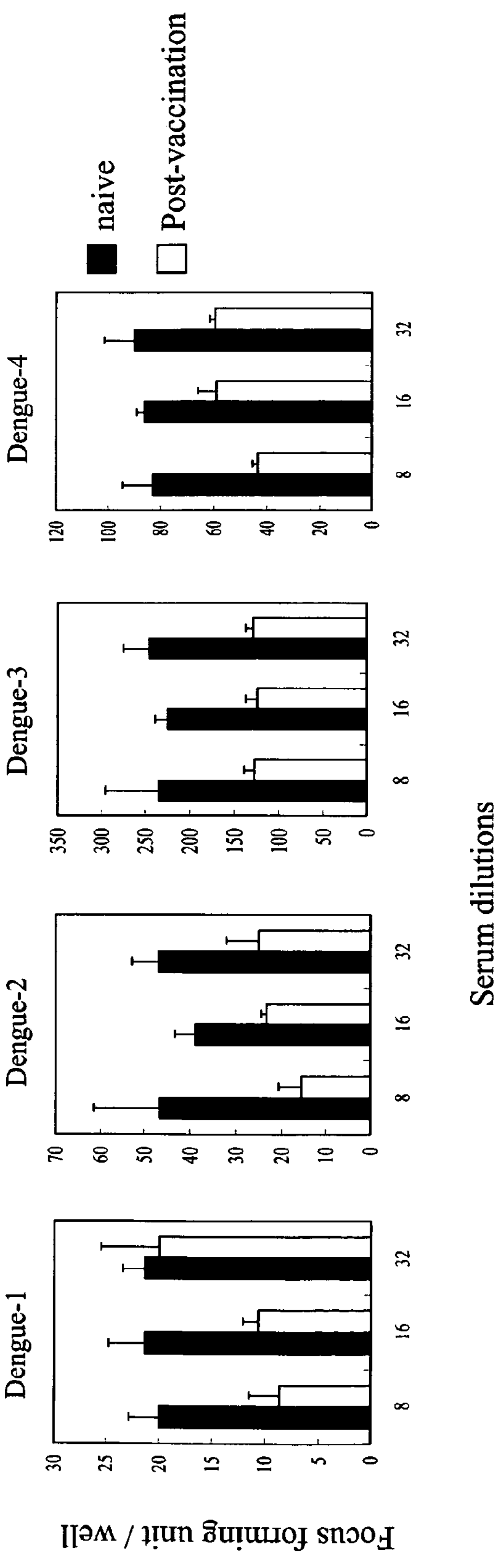
FIG. 3 shows histograms of focus-forming unit (FFU) detected when BHK cells were infected with dengue-1, dengue-2, dengue-3, and dengue-4 viruses that had been pre-mixed with various dilutions of post-vaccination sera from an animal vaccinated with a vaccine comprising DEN consensus of SEQ ID NO: 5, or pre-mixed with various dilutions of the naive sera according to embodiments of the present invention.

As shown in FIG. 3, no FFU was detected when the BHK cells were incubated with dengue-1, dengue-2, dengue-3 and dengue-4 virus that had been pre-mixed with post-immunization sera at various serum dilutions. Two to three replicates were performed in each treatment group. These results indicate that the consensus peptide of SEQ ID NO:5 is able to elicit neutralization antibody responses against four serotypes of dengue viruses in the vaccinated animals.

Example 4

Induction of Neutralizing Antibody Responses by Peptide Derived from DEN Consensus The sequence of synthetic peptide was derived from position 7 to 40 of DEN consensus of SEQ ID NO:5. Mice were initially immunized subcutaneously with 30 μg of synthetic DEN consensus peptide (SEQ ID NO:6) emulsified in complete Freund's adjuvant (CFA). The same amount of the synthetic peptide emulsified in incomplete Freund's adjuvant (IFA) was used to boost immunization on day 14 and day 28 after the initial immunization. Sera containing antibodies against the DEN consensus peptide (SEQ ID NO:6) were collected from the mice two weeks after the second boost. Naïve sera were prepared as control. The effect of vaccination was measured from the post-vaccination sera by neutralization antibody responses against four serotypes of dengue virus.

Figure 4:
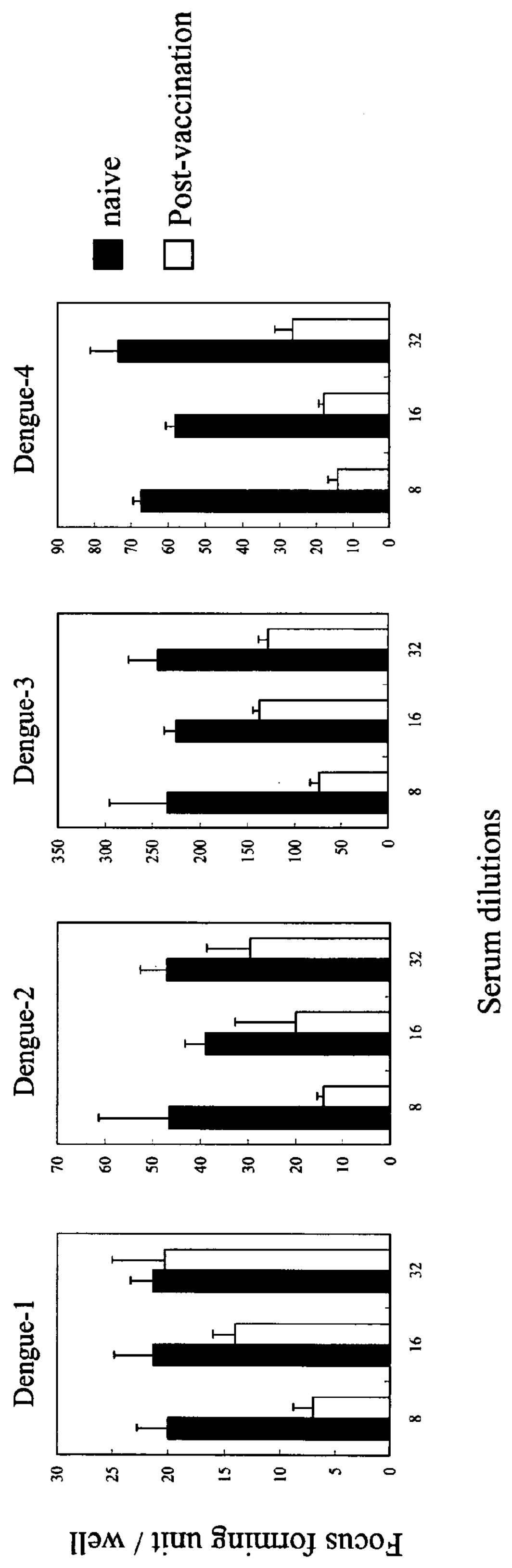
FIG. 4 shows histograms of FFUs detected when BHK cells were infected with dengue-1, dengue-2, dengue-3, and dengue-4 viruses that had been pre-mixed with various dilutions of post-vaccination sera (post-immune sera) from an animal vaccinated with a synthetic peptide of SEQ ID NO: 6, or pre-mixed with various dilutions of the naive sera according to embodiments of the present invention.

As shown in FIG. 4, significantly reduced numbers of FFU were detected when BHK cells were incubated with dengue-1, dengue-2, dengue-3, and dengue-4, respectively pre-mixed with post-immunization sera at various serum dilutions. Two to three replicates were performed in each treatment group. These results indicate that the synthetic peptide of SEQ ID NO:6 can elicit neutralization antibody responses against four serotypes of dengue viruses in the vaccinated animals.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

We claim:

1. An isolated peptide comprising SEQ ID NO:5.

2. A purified recombinant peptide comprising SEQ ID NO:5.

3. A purified synthetic peptide comprising SEQ ID NO:5.

4. The purified synthetic peptide according to claim 3 wherein said peptide comprises SEQ ID NO:6.

5. An immunogenic composition comprising a peptide of SEQ ID NO:5.

6. The immunogenic composition according to claim 5, wherein the peptide comprises SEQ ID NO:6.

7. The immunogenic composition according to claim 5, comprising about 10 μg to about 0.1 mg of the peptide per dose of administration.

8. The immunogenic composition according to claim 5 further comprising an adjuvant.

9. The immunogenic composition according to claim 5, wherein the immunogenic composition induces a neutralizing antibody against at least one dengue virus selected from the group consisting of serotypes 1, 2, 3 and 4.

10. The immunogenic composition according to claim 9, wherein the neutralizing antibody is against all four of serotypes 1, 2, 3 and 4 of dengue virus.

11. A kit comprising a vial or container and instructions, wherein said vial or container comprises the immunogenic composition of claim 5, and wherein said instructions are directed to the use of said immunogenic composition to induce an immune response in a subject.

12. A method of inducing a dengue virus-specific immune response in a subject, comprising administering to the subject an immunogenically effective amount of the immunogenic composition of claim 5, wherein said immunogenic composition induces a dengue virus-specific immune response.

13. The method according to claim 12, wherein the peptide comprises SEQ ID NO:6.

14. The method according to claim 12, wherein the immunogenic composition of claim 9 is administered to the subject two or more times.

15. A method of detecting a dengue virus infection in a subject, the method comprising:

obtaining a biological sample from the subject;

contacting the biological sample with a peptide consisting essentially of SEQ ID NO:5; and detecting the presence of an antibody in the biological sample that binds specifically to the peptide.

16. The method according to claim 15, wherein the dengue virus is at least one selected from the group consisting of serotypes 1, 2, 3, and 4.

17. A kit comprising a vial or container and instructions, wherein said vial or container comprises a peptide comprising SEQ ID NO:5, and wherein said instructions are directed to the use of said peptide to detect the dengue virus infection in the subject.

* * * * *